United States Patent [19]

Atalar

[11] Patent Number: 4,603,585
[45] Date of Patent: Aug. 5, 1986

[54] METHOD FOR REPRESENTING ELASTIC PARAMETERS OF OBJECT SURFACES

[75] Inventor: Abdullah Atalar, Ankara, Turkey

[73] Assignee: Ernst Leitz Wetzlar GmbH, Wetzlar, Fed. Rep. of Germany

[21] Appl. No.: 712,110

[22] Filed: Mar. 15, 1985

[30] Foreign Application Priority Data

Mar. 17, 1984 [DE] Fed. Rep. of Germany ....... 3409929

[51] Int. Cl.$^4$ ............................................. G01N 29/00
[52] U.S. Cl. ......................................... 73/606; 73/579
[58] Field of Search .................. 73/606, 629, 599, 579

[56] References Cited

U.S. PATENT DOCUMENTS 4,459,852  7/1984  Chubachi et al. ...................... 73/606
4,503,708  3/1985  Kino et al. ............................ 73/606

Primary Examiner—Anthony V. Ciarlante
Attorney, Agent, or Firm—Schwartz, Jeffery, Schwaab, Mack, Blumenthal & Evans

[57] ABSTRACT

A method for representing elastic parameters of object surfaces by scanning the object surface with a focused acoustic beam and detection of the interferences between the ultrasonic beams specularly reflected at the object surface and the ultrasonic beams emitted from the object surface after excitation of surface waves in which either two raster-shaped scannings of the object surface are carried out at different focus positions relative to the object surface or successive scannings are carried out with acoustic beams of different frequency. Reflection signals associated with identical raster points form a difference signal which is used for representing the image.

18 Claims, 6 Drawing Figures

METHOD FOR REPRESENTING ELASTIC PARAMETERS OF OBJECT SURFACES

BACKGROUND OF THE INVENTION

The invention relates to a method for representing elastic parameters of object surfaces by scanning the object surface with a focused acoustic beam and detecting the interference between the ultrasonic rays specularly reflected at the object surface and the ultrasonic rays emitted from the object surface after excitation of surface waves.

Scanning of an object surface by means of a focused acoustic beam can be carried out by means of an acoustic microscope operating in a reflection mode. In the normal operating mode, an acoustic lens arrangement is focused onto a certain object plane which is then scanned in a raster-patterned movement perpendicularly to the direction of propagation of the acoustic beam (x/y scanning). The signal reflected by the object is isolated from the emitted signal and used for image representation.

Another known operating mode involves scanning the object at a certain place only in the direction of propagation of the acoustic beam (z scanning). In this arrangement, therefore, the ultrasonic focus is continuously shifted into the depth of the object. The so-called V(z) curves obtained by this means are produced by interference of a specularly reflected ultrasonic beam with an ultrasonic beam which is returning to the acoustic lens arrangement, after being laterally offset, as a result of the excitation of surface waves. The respective output voltage at the acoustic transducer is a reflection signal which corresponds to the integration of the acoustic interference field over the area of the transducer. It is known that materials having different elastic parameters display a V(z) dependence which is characteristic of the material. This is why the curves can be used for identifying homogeneous layers of material.

One advantage of acoustical reflection microscopy consists in the fact that layers lying below the object surface can also be imaged if the acoustic beam is focused onto such a plane. If the beam is focused on the object surface, it is assumed that z=0 for the surface. For focus positions below the object surface, z for the surface is designated to be negative. With different negative z values, the contrasts of the acoustic images is determined by the respective local V(z) value because of the abovementioned interference phenomena. This means that the contrast of the acoustic image must contain information on elastic parameters inside the object surface. A detailed discussion of the relationships between V(z) and the acoustic image contrast is contained in J. Appl. Phys. 49 (10), pp. 5130–5139 (1978).

SUMMARY OF THE INVENTION

The present invention is directed toward providing a method by means of which the information contained in the image contrast on the distribution of elastic parameters existing in the object surface scanned can be made visible.

The method according to the invention utilizes the finding that the curve shapes obtained with the known V(z) measurements essentially depend on the type of the surface wave excited in each case. The amplitude and wavelength of this surface wave is influenced by the elastic characteristics of the material at the object point irradiated. The possible extent of the surface wave is affected by the magnitude of z. In this manner, different amplitudes and phase relationships are obtained for the ultrasonic beams which are generated by the surface waves, received by the acoustic lens arrangement, and which interfere with the rays specularly reflected at the object surface. The V(z) curves show typical interference maxima and minima.

This influence on the imaging rays by processes occurring in a thin surface layer of the object is superimposed to a more or less large degree on every acoustic image representation and, as already mentioned, influences the contrast of the image obtained from a certain z plane. According to the invention, the z-independent image signals are suppressed by taking an image from two object planes and determining the difference between them. The acoustic image then shows the change in contrast between the two images originally taken. The change in contrast thus made visible is a direct image of the distribution of the elastic parameters in the object surface.

A more accurate examination of the parameters determining the interference maxima and minima in the V(z) curves shows that these maxima and minima also depend on the frequency of the acoustic beams used for the examination. In particular, it is found that the shape of the curve depends on the product of the ultrasonic frequency f and the relative distance z of the ultrasonic focus from the object surface. For this reason, the invention utilizes the further finding that the elastic parameters can be represented also by keeping z constant and varying the frequency f. Changing the frequency instead of the position is much simpler and can be carried out more rapidly. In addition, it has the advantage that, when the difference is found, the image components to be suppressed originate from the same object plane. In addition, the area of extent of the surface wave is identical with both measurements so that the change in contrast shown has an even closer relationship to the locally existing elastic properties of the material of the object surface.

Both the method involving position change and the method involving frequency change can be carried out in such a manner that initially in each case the object is completely scanned and the images obtained are stored. However, this requires a relatively large expenditure for providing the necessary memory capacity. In addition, very high demands are made on the quality of the image taking since the parameters, which are constant during the image taking, must not change during the scanning which varies with time. For this reason, it is of advantage to carry out the switching-over operations at each scanning point before going to the next scanning point.

When changing the frequency, an additional problem arises from the fact that the total gain in the acoustic microscope used for taking the image varies as a function of the ultrasonic frequency. In order to obtain complete signal cancellation with the frequency-independent parts of the object, the amplitudes of the two images must be suitably weighted in each case.

BRIEF DESCRIPTION OF THE DRAWINGS

In the text which follows, the method according to the invention is explained in greater detail with the assistance of the drawing. In particular, advantageous circuit arrangements for carrying out the method are specified. In detail.

DETAILED DESCRIPTION OF THE PREFERRED EMBODIMENTS

Figure 1:
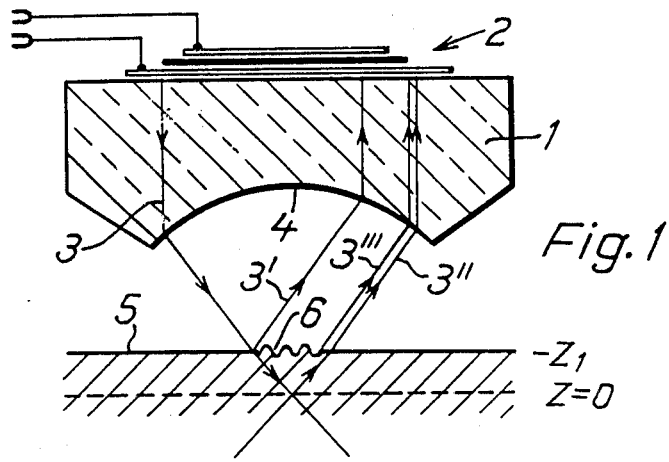
FIG. 1 shows an acousto-microscopic reflection arrangement and the diagrammatic optical path.

FIG. 1 shows a greatly simplified representation of an acousto-microscopic reflection arrangement. It consists of an acoustic lens 1 including a piezoelectric transmitter 2. This is used first for generating a planar ultrasonic wave front indicated by the ray 3. The spherical cavity 4 in the acoustic lens focuses the acoustic beam onto the object 5 to be examined. The intermediate space between the acoustic lens 1 and the object 5 is filled with an immersing medium, not shown in this Figure.

The object surface is assumed to be at $-z_1$ and the focus of the acoustic lens 1 in the plane $z=0$. The ray 3 impinging on the object surface is specularly reflected at the surface as ray 3'. A part of the ray 3 penetrates into the object and is reflected back out of the focal plane as ray 3" into the acoustic lens. Another ray 3''' is generated by the surface wave 6. Within the lens body, all three rays directed towards the acoustic lens correspond to planar soundwaves reaching the transmitter with a mutual offset in phase and interfering with each other. The transmitter integrates the acoustic field and converts it into electric signals.

The events occurring during the irradiation of the object surface will be explained diagrammatically with the aid of the optical path shown in FIG. 1. Only rays falling into the area of the aperture of the acoustic lens are used. The return rays 3', 3", and 3''' mutually interfere and constitute a reflection signal.

It should be noted in this regard that the events connected with the generation of the surface wave 6 are very complex. Also, as shown in the illustration, the area from which rays 3''' can be produced depends on the negative z position of the object surface. The rays 3" are very strongly affected by a layer structure located between the object surface and the focal plane. This is why V(z) curves react very sensitively to variations in layer thickness.

Clearly, the method operating with frequency switching is hardly influenced by the layer structure below the object surface. Although the change in frequency influences the depth of penetration of the ray 3 and the focus position, the changes in the ray 3" are much smaller than with a change in position. However, the influence of the change in frequency on the depth of penetration and on the wavelength of the surface wave 6 and thus on the ray 3''' is considerable. For this reason, the difference signal after frequency switching, formed in accordance with the invention, reacts also to smaller changes in the elastic parameters in the object surface. Therefore, this method is more sensitive.

Figure 2:
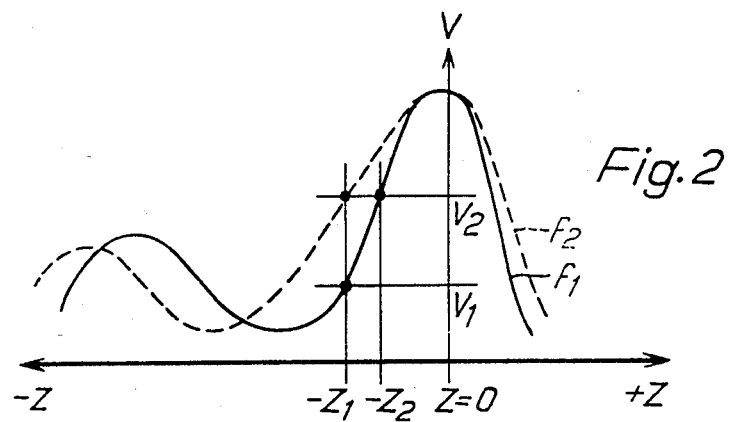
FIG. 2 shows V(z) curves diagrammatically for various frequencies.

FIG. 2 shows the typical variation of a V(z) curve. No interference maxima or minima whatever are observed for positive z values. These appear only for negative z values. The continuous curve is for a frequency $f_1$ and the dashed curve is for a frequency $f_2$. The diagram depicts the dependence of individual signal values V on a change in position or a change in frequency, respectively.

If an object surface is arranged at a distance $-z_1$ from the focal plane and a frequency $f_1$ is used, a value $v_1$ is measured. If then the frequency is changed into $f_2$ at the same object position, the measured value will change to $V_2$. The same value $V_2$ is found if frequency $f_1$ is used in object position $-z_2$. The signal change can also be considered to have resulted if the frequency $f_1$ had been maintained but the object moved to position $-z_2$. According to the invention, the difference $V_2-V_1$ is formed and used for image representation. Thus, the highest-contrast representation of the elastic parameters is obtained from the z adjustments in which the V(z) curves have the steepest slope.

The method of frequency switching can also be carried out in the object position $z=0$. In this case, the differential image shows only the frequency-dependent parts of the object. In this case, the frequency-dependent depth of penetration of the surface wave becomes significant. The resultant image is therefore very sensitively dependent on a layer thickness structure which is of the order of magnitude of the depth of penetration of the surface wave.

Figure 3:
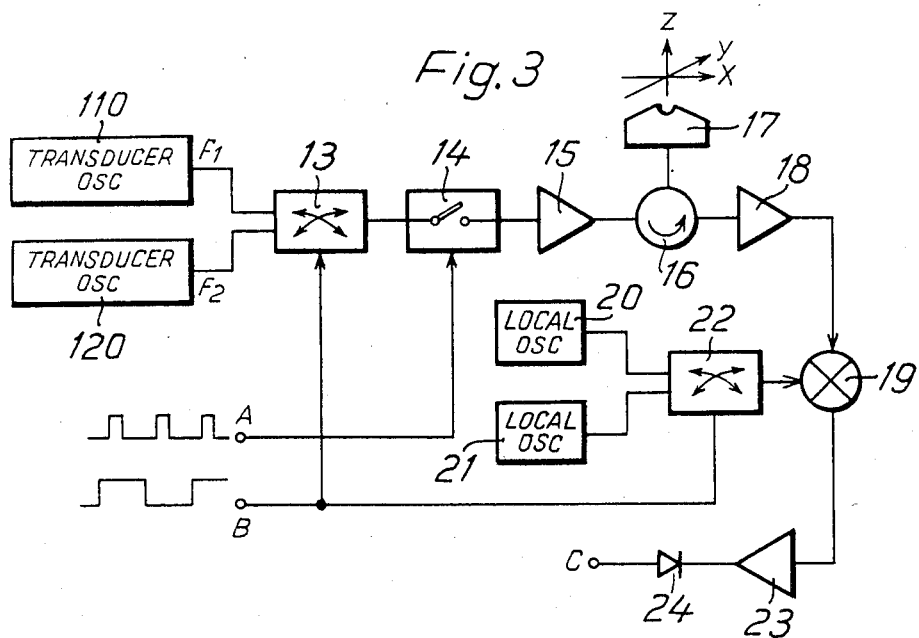
FIG. 3 shows a circuit arrangement for alternating frequency switching.

The circuit arrangement shown in FIG. 3 provides the possibility of an alternating switching between operating frequencies $f_1$ and $f_2$. It consists of two transducer oscillators 110 and 120 for generating high-frequency oscillations having frequencies $f_1$ and $f_2$. These oscillations are alternately switched to the following line by a following two-way pin switch 13. The pin switch 13 is controlled by rectangular pulses which are fed into the circuit arrangement via an input B. Another pin switch 14 generates from the trains of oscillations short pulses having the frequencies $f_1$, $f_2$. The switch 14 is controlled by rectangular pulses which are fed into the circuit via an input A. The switching signals A are displaced in time by a small amount with respect to the switching edges of the signals B. In practice, the repetition frequency of the switching signals A is about 500 kHz.

The $f_1$ and $f_2$ pulses are amplified in a power amplifier 15 and are successively conducted via a circulator 16 to the piezoelectric transmitter, not shown, of an acoustic lens 17. After that, the input line is blocked by the circulator 16 so that the $f_1$ and $f_2$ measurement signals received by the acoustic lens 17 can be fed undisturbed into the receiver section of the circuit arrangement.

The receiver section contains a preamplifier 18 and a subsequent superheterodyne circuit. This circuit consists of a mixing element 19, two local oscillators 20, 21, a two-way pin switch 22 and an intermediate-frequency amplifier 23. In a superheterodyne circuit, the frequency of the local oscillator must be tuned in such a way that the frequency difference between the local oscillator frequency and the transducer oscillator frequency is equal to the intermediate frequency $f_M$ of the intermediate-frequency amplifier 23. In the proposed system, this is achieved by inserting two local oscillators 20, 21 having the frequencies $f_1 \pm f_M$ and $f_2 \pm f_M$ which, via the pin switch 22, become active at the mixing element 19 with the same alternating switching sequence B as is used to switch the transmitter oscillators 11, 12. In this manner, the same frequency is always present at the input of the intermediate-frequency amplifier 23. The signal output C is terminated with a high-frequency diode 24 for generating a video signal.

At the signal output C of the intermediate-frequency amplifier 23 appear pulses the amplitude of which represents the acousto-microscopic measurement signal for two different frequencies in alternating sequence. Since the repetition frequency of the pulses is relatively high and a relatively slow mechanical scanning method (x/y scan) is used, the successive pulses can be considered to have originated from the same object point.

Figure 4:
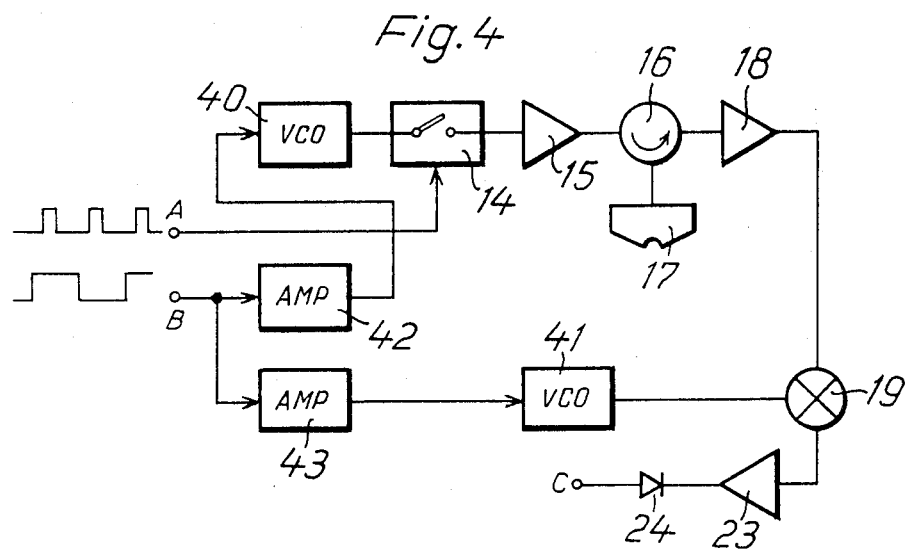
FIG. 4 shows another circuit arrangement for alternating frequency switching.

In the circuit arrangement shown in FIG. 4, the two transducer oscillators and the two local oscillators are in each case replaced by a voltage-controlled oscillator (VCO) 40, 41. The input signals for controlling the frequency of the oscillators 40, 41 are derived from the frequency switching signal B. The direct-voltage level and the amplitude of the rectangular waves are tuned by interposed amplifiers 42, 43 in such a manner that the frequency difference of the two oscillators is equal to the intermediate frequency $f_M$ of the intermediate-frequency amplifier 23.

Figure 5:
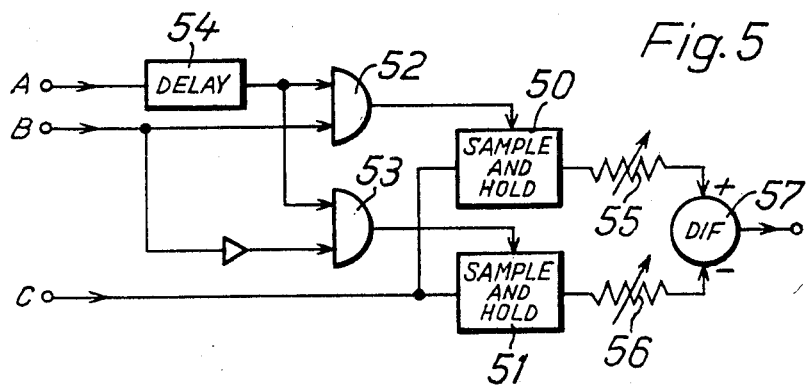
FIG. 5 shows a circuit arrangement for generating the amplitude difference including weighting of the measurement pulses.
Figure 6:
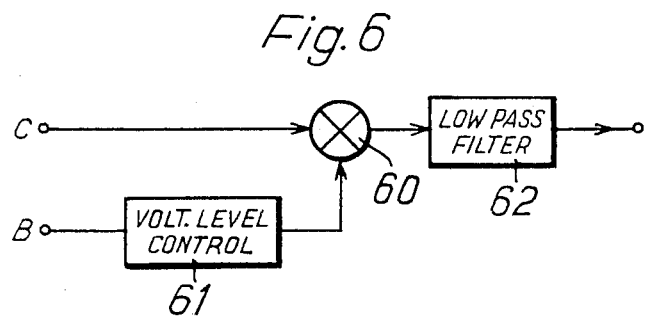
FIG. 6 shows another circuit arrangement for forming the difference.

For generating the amplitude difference of the successive $f_1$ and $f_2$ measurement signal pulses, one of the circuit arrangements shown in FIGS. 5 and 6 can be used.

In FIG. 5, two sample-and-hold components 50, 51 are inserted into the line C carrying the measurement signal, in such a manner that one samples only the $f_1$ measurement pulses and the other one only the $f_2$ measurement pulses. For this purpose, the sample-and-hold components 50, 51 are enabled by two AND gates 52, 53 as a function of the switching signals A and B. The signal A can also be delayed in a delay unit 54 by the transit time between the excitation signal at the acoustic lens 17 and reception of the measurement signal.

The analog measurement signals produced at the output of the sample-and-hold components 50, 51 can be weighted with the assistance of adjustable potentiometers 55, 56. This weighting can be tuned in such a manner that the subsequent subtraction in the difference forming circuit 57 results in 0 for all frequency-independent parts of the object. The necessary weighting can be manually adjusted by observing a line scan (x scan).

In the circuit arrangement shown in FIG. 6, the $f_1$ and $f_2$ measurement pulses are input into a four-quadrant analog multiplier 60. The multiplier is controlled by the frequency switching signal B, the direct-voltage level of which is in turn controlled in a voltage level control element 61 in order to be able to set positive and negative amplitudes for the rectangular wave. In the multiplier 60, the $f_1$ measurement pulses are multiplied by the positive amplitude value of the signal B and the $f_2$ measurement pulses are multiplied by the negative amplitude value of the signal B. Thus the measurement pulses can be given different weighting by shifting the direct-voltage level.

At the output of the multiplier 60, a pulse sequence of alternately positive and negative measurement values is produced which subsequently passes through a low-pass filter 62. This results in the same effect as a difference forming circuit.

Naturally, the analog difference forming circuits according to FIGS. 5 and 6 can also be used for a measurement signal sequence produced with an alternating z position setting at the signal input C. In this arrangement, the control signal B defines the respective focus position of the acoustic lens 17 which is suitably generated by appropriate z adjustment of the object stage when the lens is performing the x/y scanning movement. A suitable adjustment is, for example, a piezoelectric adjustment of the object stage in the z direction.

For many applications, the measurement signals can also be suitably converted in each case into digital values and the forming of the difference and possible weighting of the signals carried out in a computer. This will be advantageous especially if the object scanning from one plane or at one frequency is to be followed also by automatic image analysis.

While several embodiments of the invention have been described, it will be understood that it is capable of further modification, and this application is intended to cover any variations, uses, or adaptations of the invention, following in general the principles of the invention and including such departures from the present disclosure as to come within the knowledge or customary practice in the art.

What is claimed is:

1. A method of representing elastic parameters of the surface of an object comprising the steps for each point of a predetermined pattern of points on said surface of:
    (a) directing a first acoustic beam having a first focus position at said each point;
    (b) sensing a first reflection signal;
    (c) directing a second acoustic beam having a second focus position different from said first focus position at said each point;
    (d) sensing a second reflection signal;
    (e) deriving a difference signal having a value indicative of the difference between said first and second reflection signals; and
    (f) using said difference signal to represent said elastic parameters at said each point.

2. A method as claimed in claim 1, wherein said steps (a)–(f) are all executed for each point before execution proceeds to a next point.

3. A method as claimed in claim 2, wherein said one of first and second reflection signals for each point is multiplied by a weighting factor prior to derivation of said difference signal for said each point.

4. A method as claimed in claim 3, wherein said first and second focus positions are selected to maximize said difference signal at at least one of said points.

5. A method as claimed in claim 2, wherein said first and second reflection signals are fed directly to a difference-forming circuit.

6. A method as claimed in claim 1, wherein said steps (a) and (b) are both executed for every point in said pattern before execution of any of said steps (c)–(f), and then step (c) and (d) are both executed for every point in said pattern before execution of either of said steps (e) and (f).

7. A method as claimed in claim 6 wherein each of said first reflection signals and each of said second reflection signals are stored.

8. A method as claimed in claim 7 wherein one of said first and second reflection signals for each point is multiplied by a weighting factor prior to derivation of said difference signal for said each point.

9. A method as claimed in claim 6 wherein said first and second focus positions are selected to maximize said difference signal at at least one of said points.

10. A method of representing elastic parameters of the surface of an object comprising the steps for each point of a predetermined pattern of points on said surface of:

(a) directing a first acoustic beam having a first frequency at said each point;

(b) sensing a first reflection signal;

(c) directing a second acoustic beam having a second frequency different from said first frequency at said each point;

(d) sensing a second reflection signal;

(e) deriving a difference signal having a value indicative of the difference between said first and second reflection signals; and (f) using said difference signal to represent said elastic parameters at said each point.

11. A method as claimed in claim 10 wherein said steps (a)–(f) are all executed for said each point before execution proceeds to a next point.

12. A method as claimed in claim 11 wherein one of said first and second reflection signals for each point is multiplied by a weighting factor prior to derivation of said difference signal for said point.

13. A method as claimed in claim 12 wherein said first and second frequencies are selected to maximize said difference signal at at least one of said points.

14. A method as claimed in claim 11 wherein said first and second reflection signals are fed directly to a difference-forming circuit.

15. A method as claimed in claim 10 wherein said steps (a) and (b) are both executed for every point in said pattern before execution of any of said steps (c)–(f), and then said steps (c) and (d) are executed for every point in said pattern before execution of either of said steps (e) and (f).

16. A method as claimed in claim 15 wherein each of said first reflection signals and each of said second reflection signals are stored.

17. A method as claimed in claim 16 wherein one of said first and second reflection signals for each point is multiplied by a weighting factor prior to derivation of said difference signal for said point.

18. A method as claimed in claim 15 wherein said first and second frequencies are selected to maximize said difference signal at at least one of said points.

* * * * *